United States Patent [19]

Shahidi

[11] Patent Number: 6,167,296
[45] Date of Patent: Dec. 26, 2000

[54] METHOD FOR VOLUMETRIC IMAGE NAVIGATION

[75] Inventor: Ramin Shahidi, San Francisco, Calif.

[73] Assignee: The Board of Trustees of the Leland Stanford Junior University, Stanford, Calif.

[21] Appl. No.: 09/411,363

[22] Filed: Sep. 30, 1999

Related U.S. Application Data

[63] Continuation of application No. 08/884,289, Jun. 27, 1997, abandoned.
[60] Provisional application No. 60/020,664, Jun. 28, 1996.

[51] Int. Cl.$^7$ ...................................................... A61B 5/00
[52] U.S. Cl. .......................... 600/427; 600/429; 600/117; 600/439; 606/130
[58] Field of Search ............................ 606/130; 600/407, 600/411, 417, 424, 425, 427, 429, 439, 109, 117

[56] References Cited

U.S. PATENT DOCUMENTS

| Re. 30,397 | 9/1980 | King . |
| 4,583,538 | 4/1986 | Onik et al. . |
| 4,770,182 | 9/1988 | Damadian et al. . |
| 4,945,478 | 7/1990 | Merickel et al. . |
| 4,977,505 | 12/1990 | Pelizzari et al. . |
| 5,070,401 | 12/1991 | Salvati et al. . |
| 5,078,140 | 1/1992 | Kwoh . |
| 5,222,499 | 6/1993 | Allen et al. . |
| 5,230,338 | 7/1993 | Allen et al. . |
| 5,261,404 | 11/1993 | Mick et al. . |
| 5,299,253 | 3/1994 | Wessels . |

(List continued on next page.)

OTHER PUBLICATIONS

Anon J.B., et al., "Computer–Assisted Endoscopic Sinus Surgery—Current Experience and Future Developments", *Operative Techniques in Otolaryngology* (1995) 6 (3):163–170.

Ault, T. and Siegel, M.W., "Frameless Patient Registration Using Ultrasonic Imaging: A Preliminary Study" *J. Image Guid. Surg.* (1995) 1:94–102.

Bainville, E., et al., "Computer Generated Visual Assistance During Retroperitoneoscopy" *Comput. Biol. Med.* (1995) 25(2):165–171.

Brady, M.L., et al., "Interactive Navigation Inside 3D Radiological Images" IEEE (1995) pp. 33–40.

Brett, P., et al., "Automatic Surgical Tool for Penetrating Flexible Tissues" *IEEE Engin. in Med. and Biol.* (1995) May/Jun.:264–270.

Burckhardt, C.W., et al., "Stereotactic Brain Surgery" *IEEE Engin. in Med. and Biol.* (1995) May/Jun.:314–317.

(List continued on next page.)

*Primary Examiner*—Ruth S. Smith
*Attorney, Agent, or Firm*—Peter J. Dehlinger; Francis H. Lewis, Jr.

[57] ABSTRACT

A surgical navigation system has a computer with a memory and display connected to a surgical instrument or pointer and position tracking system, so that the location and orientation of the pointer are tracked in real time and conveyed to the computer. The computer memory is loaded with data from an MRI, CT, or other volumetric scan of a patient, and this data is utilized to dynamically display 3-dimensional perspective images in real time of the patient's anatomy from the viewpoint of the pointer. The images are segmented and displayed in color to highlight selected anatomical features and to allow the viewer to see beyond obscuring surfaces and structures. The displayed image tracks the movement of the instrument during surgical procedures. The instrument may include an imaging device such as an endoscope or ultrasound transducer, and the system displays also the image for this device from the same viewpoint, and enables the two images to be fused so that a combined image is displayed. The system is adapted for easy and convenient operating room use during surgical procedures.

3 Claims, 15 Drawing Sheets

U.S. PATENT DOCUMENTS

| | | |
|---|---|---|
| 5,313,306 | 5/1994 | Kuban et al. . |
| 5,337,732 | 8/1994 | Grundfest et al. . |
| 5,363,475 | 11/1994 | Baker et al. . |
| 5,389,101 | 2/1995 | Heilbrun et al. . |
| 5,417,210 | 5/1995 | Funda et al. . |
| 5,419,320 | 5/1995 | Kawaguchi et al. . |
| 5,454,371 | 10/1995 | Fenster et al. . |
| 5,458,126 | 10/1995 | Cline et al. . |
| 5,491,510 | 2/1996 | Gove . |
| 5,531,520 | 7/1996 | Grimson et al. . |
| 5,540,229 | 7/1996 | Collet-Billon et al. . |
| 5,546,807 | 8/1996 | Oxaal et al. . |
| 5,562,095 | 10/1996 | Downey et al. . |
| 5,572,999 | 11/1996 | Funda et al. . |
| 5,585,813 | 12/1996 | Howard . |
| 5,604,848 | 2/1997 | Harada et al. . |
| 5,608,849 | 3/1997 | King, Jr. . |
| 5,611,025 | 3/1997 | Lorensen et al. . |
| 5,622,170 | 4/1997 | Schulz . |
| 5,671,381 | 9/1997 | Stransnick et al. . |
| 5,682,886 | 11/1997 | Delp et al. . |
| 5,704,897 | 1/1998 | Truppe . |
| 5,740,802 | 4/1998 | Nafis et al. . |
| 5,772,594 | 6/1998 | Barrick . |
| 5,776,050 | 7/1998 | Chen et al. . |
| 5,781,195 | 7/1998 | Marvin . |
| 5,797,849 | 8/1998 | Vesely et al. . |
| 5,800,352 | 8/1998 | Ferre et al. . |
| 5,815,126 | 9/1998 | Fan et al. . |
| 5,833,608 | 11/1998 | Acker . |
| 5,833,627 | 11/1998 | Shmulewitz et al. . |
| 5,836,954 | 11/1998 | Heilbrun et al. . |
| 5,842,473 | 12/1998 | Fenster et al. . |
| 5,855,553 | 1/1999 | Tajima et al. . |
| 5,868,673 | 2/1999 | Vesely . |
| 5,871,018 | 2/1999 | Delp et al. . |
| 5,882,206 | 3/1999 | Gillio . |
| 5,887,121 | 3/1999 | Funda et al. . |
| 5,891,034 | 4/1999 | Bucholz . |
| 5,892,538 | 4/1999 | Gibas . |
| 6,016,439 | 1/2000 | Acker .................................. 600/411 |

OTHER PUBLICATIONS

Chang, Y–K., et al., "Visualizing the Anatomical–Functional Correlation of the Human Brain" *SPIE* (1995) 2410:32–41.

Charles, S., "Dexterity Enhancement for Surgery" MRCAS (1994) pp. 145–160.

Chinzei, K., et al., "Quantitative Integration of Multimodality Medical Images" *SPIE* (1992) 1808:187–195.

Cinquin, P., et al., "Computer Assisted Medical Interventions" *IEEE Engin. in Med. and Biol.* (1995) May/Jun.:254–263.

Cohen, D.S., et al., "Effects of coregistration of MR to CT images on MR stereotactic accuracy" *J. Neurosurg.* (1995) 82:772–779.

Colchester, A.C.F, et al., "Craniotomy Simulation and Guidance Using a Stereo Video Based Tracking System (VISLAN)" *SPIE* (1994) 2359:541–551.

Collins, D.L., et al., "An Automated 3D non–linear image deformation procedure for Determination of Gross Morphometric Variability in Human Brain" *SPIE* (1994) 2359:180–190.

Davey, B.L.K., et al., "Multimodality Interactive Stereoscopic Image–Guided Neurosurgury" *SPIE* (1994) 2359:526–536.

Ehricke, H–H., et al., "Interactive 3D–graphics workstations in stereotaxy: Clinical requirements, algorithms and solutions" *SPIE* (1992) 1808:548–558.

Finlay, P.A., and Ornstein, M.H., "Controlling the Movement of a Surgical Laparoscope" *IEEE Engin. in Med. and Biol.* (1995) May/Jun.:289–291.

Gee, J.C., et al., "Matching Structural Images of the Human Brain Using Statistical and Geometrical Image Features" *SPIE* (1994) 2359:191–204.

Giorgi, C., et al., "Robot–Assisted Microscope for Neurosurgery" *J. Image Guid. Surg.* (1995) 1:158–163.

Goble, J.C., et al., "A Real–Time System for 3D Neurosurgical Planning" *SPIE* (1994) 2359:552–563.

Grimson, E., et al., "Automated Registration for Enhanced Reality Visualization in Surgery" *AAAL Spring Symposium* (1994) pp. 26–29.

Hamadeh, A., et al., "Anatomy Based Multi–modal Medical Image Registration for Computer Integrated Surgery" *SPIE* (1994) 2355:178–188.

Henri, C. et al., "Towards Frameless Stereotaxy: Anatomical–Vascular Correlation and Registration" *SPIE* (1992) 1808:214–224.

Hill, D.L.G., et al., "Visualisation of multi–modal images for the planning of skull base surgery" *SPIE* (1992) 1808:564–573.

Hill, D.L.G., et al., "Voxel Similarity Measures for Automated Image Registration" *SPIE* (1994) 2359:205–216.

Horstmann, G.A., et al., "Micro–Stereometry: A Frameless Computerized Navigating System for Open Microsurgery" *Comput. Med. Imaging and Graphics* (1994) 18(4):229–233.

Jiang, H., et al., "A New Approach to 3–D Registration of Multimodality Medical Images by Surface Matching" *SPIE* (1992) 1808:196–213.

Kazanzides, P., et al., "An Integrated System for Cementless Hip Replacement" *IEEE Engin. in Med. and Biol.* (1995) May/Jun.:307–313.

Kienzle III, T.C., et al., "Total Knee Replacement" *IEEE Engin. in Med. and Biol.* (1995) May/Jun.:301–306.

Kikinis, R., et al., "Interactive visualization and manipulation of 3D reconstructions for the planning of surgical procedures" *SPIE* (1992) 1808:559–563.

Kikinis, R., et al., "Image guidance techniques for neurosurgery" *SPIE* (1994) 2359:537–540.

Lea, J.T., et al., "Diagramming Registration Connectivity and Structure" *IEEE Engin. in Med. and Biol.* (1995) May/Jun.:271–278.

Liu, A., et al., "Volume registration using the 3D core" *SPIE* (1994) 2359:217–226.

Matz, P., et al., "Cavernous Malformations: Results of Image–Guided Resection" *J. Image Guid. Surg.* (1995) 1:273–279.

Merloz et al., "Pedicle Screw Placement Using Image Guided Techniques" *Clin. Orthop.* (1998) 354:39–48.

Morita, A. and Kelly, P.J., "Resection of Intraventricular Tumors via a Computer–assisted Volumetric Stereotactic Approach" *Neurosurgery* (1993) 32(6):920–927.

Nolte, L., et al., "A Novel Approach to Image Guided Spine Surgery" *SPIE* (1994) 2359:564–573.

Peifer, J.W., et al., "3–D registration and visualization of reconstructed coronary arterial trees on myocardial perfusion distributions" *SPIE* (1992) 1808:225–234.

Pérault, C., et al., "Automatic superimposition of CT and SPET immunoscintigraphic images in the pelvis" *SPIE* (1992) 1808:235–240.

Sciabassi, J., et al., "NeuroNet: Collaborative Intraoperative Guidance and Control" *IEEE Computer Graphics and Applications* (1996) pp. 39–45.

Simon, D.A., et al., "Techniques for Fast and Accurate Intrasurgical Registration" *J. Image Guid. Surg.* (1995) 1:17–29.

Taneja, U., et al., "Evaluating the accuracy of three–dimensional image registration algorithms used in multimodal image fusion" *SPIE* (1994) 2359:238–250.

Taylor, R.H., et al., "A Telerobotic Assistant for Laproscopic Surgery" *IEEE Engin. in Med. and Biol.* (1995) May/Jun.:279–288.

Tebo, S.A., et al., "An Optical 3D Digitizer for Frameless Stereotactic Surgery" *IEEE Computer Graphics and App.* (1996) Jan.:55–63.

van den Elsen, P.A., et al., Image Fusion using geometrical features *SPIE* (1992) 1808:172–186.

van den Elsen, P.A., et al., "Medical Image Matching—A Review with Classification" *IEEE Engin. in Med. and Biol.* (1993) Mar.:26–39.

van den Elsen, P.A., et al., "Grey value correlation techniques used for automatic matching of CT and MR brain and spine images" *SPIE* (1994) 2359:227–237.

Wells, III, W.M., et al., "Multi–modal volume registration by maximization of mutual information" *Med. Image Analysis* (1996) 1(1):35–51.

Zamorano, L., et al., "Computer–Assisted Neurosurgery System: Wayne State University Hardware and Software Configuration" *Comput. Med. Imaging and Graphics* (1994) 18(4):257–271.

Zhuang, H., et al., "Practical Fusion Algorithms for Rotation Matrices: A Comparative Study" *J. of Robotic Sys.* (1992) 9(7):915–931.

METHOD FOR VOLUMETRIC IMAGE NAVIGATION

CROSS REFERENCE TO RELATED APPLICATIONS

This application is a continuation of application Ser. No. 08/884,289, filed Jun. 27, 1997 now abandoned.

This application claims the benefit of U.S. Provisional Application Ser. No. 60/020,664 filed Jun. 28, 1996. This Provisional Application Ser. No. 60/020,664 is hereby incorporated by reference in its entirety into the present application.

BACKGROUND OF THE INVENTION

1. Field of the Invention

This invention pertains generally to systems and methods for generating images of three dimensional objects for navigation purposes, and more particularly to systems and methods for generating such images in medical and surgical applications.

2. Description of the Background Art

Precise imaging of portions of the anatomy is an increasingly important technique in the medical and surgical fields. In order to lessen the trauma to a patient caused by invasive surgery, techniques have been developed for performing surgical procedures within the body through small incisions with minimal invasion. These procedures generally require the surgeon to operate on portions of the anatomy that are not directly visible, or can be seen only with difficulty. Furthermore, some parts of the body contain extremely complex or small structures and it is necessary to enhance the visibility of these structures to enable the surgeon to perform more delicate procedures. In addition, planning such procedures requires the evaluation of the location and orientation of these structures within the body in order to determine the optimal surgical trajectory.

New diagnostic techniques have been developed in recent years to obtain images of internal anatomical structures. These techniques offer great advantages in comparison with the traditional X-ray methods. Newer techniques include microimpulse radar (MIR), computer tomography (CT) scans, magnetic resonance imaging (MRI), positron emission tomography (PET), ultrasound (US) scans, and a variety of other techniques. Each of these methods has advantages and drawbacks in comparison with other techniques. For example, the MRI technique is useful for generating three-dimensional images, but it is only practical for certain types of tissue, while CT scans are useful for generating images of other anatomical structures. Ultrasound scanning, in contrast, is a relatively rapid procedure; however it is limited in its accuracy and signal-to-noise ratio.

The imaging problem is especially acute in the field of neurosurgery, which involves performing delicate surgical procedures inside the skull of the patient. The above techniques have improved the surgeon's ability to locate precisely various anatomical features from images of structures within the skull. However this has only limited usefulness in the operating room setting, since it is necessary to match what the surgeon sees on the 2D image with the actual 3D patient on the operating table. The neurosurgeon is still compelled to rely to a considerable extent on his or her knowledge of human anatomy.

The stereotactic technique was developed many years ago to address this problem. In stereotactic surgery, a frame of reference is attached to the patient's head which provides reference points for the diagnostic images. The device further includes guides for channeling the surgical tool along a desired trajectory to the target lesion within the brain. This method is cumbersome and has the drawback that the surgeon cannot actually see the structures through which the trajectory is passing. There is always the risk of damage to obstacles in the path of the incision, such as portions of the vascular or ventricular system. In essence, with previous neurosurgical techniques the surgeon is in the position much like that of a captain piloting a vessel traveling in heavy fog through waters that have many hazards, such as shoals, reefs, outcroppings of rocks, icebergs, etc. Even though the captain may have a very good map of these hazards, nevertheless there is the constant problem of keeping track of the precise location of the vessel on the map. In the same way, the neurosurgeon having an accurate image scan showing the structures within the brain must still be able to precisely locate where the actual surgical trajectory lies on the image in order to navigate successfully to the target location. In the operating room setting, it is further necessary that this correlation can be carried out without interfering with the numerous other activities that must be performed by the surgeon.

The navigation problem has been addressed in U.S. Pat. No. 5,383,454, issued Jan. 24, 1995 (Bucholz). This patent describes a system for indicating the position of a surgical probe within a head on an image of the head. The system utilizes a stereotactic frame to provide reference points, and to provide means for measuring the position of the probe tip relative to these reference points. This information is converted into an image by means of a computer.

U.S. Pat. No. 5,230,623, issued Jul. 27, 1993 (Guthrie), discloses an operating pointer whose position can be detected and read out on a computer and associated graphics display. The pointer can also be used as a "3D mouse" to enable the surgeon to control the operation of the computer without releasing the pointer.

U.S. Pat. No. 5,617,857, issued Apr. 8, 1997 (Chader et al.) sets forth an imaging system and method for interactively tracking the position of a medical instrument by means of a position-detecting system. The pointer includes small light-emitting diodes (LED), and a stationary array of radiation sensors is provided for detecting pulses emitted by these LED's and utilizing this information to ascertain dynamically the position of the pointer. Reference is made also to U.S. Pat. No. 5,622,170, issued Apr. 22, 1997 (Schulz), which describes a similar system connected to a computer display for displaying the position of an invasive surgical probe relative to a model image of the object being probed (such as a brain).

U.S. Pat. No. 5,531,227, issued Jul. 2, 1996 (Schneider) explicitly addresses the problem recognized in many other references that it is desirable to provide a real time display of a surgical probe as it navigates through the brain. This patent describes a system for providing images along the line of sight of the surgeon in a dynamic real-time fashion. In this system the images that are displayed are resliced images from a three-dimensional data reconstruction which are sections or slices orthogonal to the line of sight, taken at various positions along this line specified by the user. Thus, while the viewpoint for the line of sight is always external to the body, the sectional planes that are used to define the virtual images may constitute various slices through the body chosen by the surgeon. These images may be superimposed on actual images obtained by an image recording device directed along the line of sight such as a video camera attached to the surgeon's head, and the composite images may be displayed.

The systems described above attempt to address the navigation problem in various ways, and they all have the common drawback of requiring a certain level of abstract visualization by the surgeon during an operating room procedure. When the surgeon is proceeding through the brain toward a target tumor or lesion, it is desirable to be fully aware of all of the structures around the surgical trajectory. With previous systems the displays that are presented do not provide all of this information in a single convenient real-time display, and they require the viewer to piece together and re-orient the displayed information to obtain a mental picture of the surrounding structures. These are serious practical disadvantages in an operating room setting. What is absent from previous systems is a 3D display that shows, in a real-time view, the various structures looking ahead from the surgical probe along a line of sight into the brain in three and two dimensions, including structures hidden by other features.

SUMMARY OF THE INVENTION

The present invention provides an improved system and method for displaying 3D images of anatomical structures in real time during surgery to enable the surgeon to navigate through these structures during the performance of surgical procedures. This system is also useful in planning of surgical procedures. The system includes a computer with a display and input devices such as a keyboard and mouse. The system also includes a position tracking system that is connected both to the computer and also to the surgical probes or other instruments that are used by the surgeon. The position tracking system provides continual real time data to the computer indicating the location and orientation of the surgical instrument in use. The computer further includes a memory containing patient data produced by imaging scans, such as CT or MRI scans, from which 2-dimensional and 3-dimensional images of the anatomical structure may be generated. Means are provided for registration of these images with respect to the patient.

The computer memory is further provided with programs that control the generation of these anatomical images. These programs include software for segmentation of the scan images to identify various types of structures and tissues, as well as the reconstruction of 2D and 3D images from the scan data. This software allows these images to be displayed with various magnifications and orientations, and with various sectional views produced by slice planes in various locations and orientations, all controlled by the surgeon.

This image-generating software has the important feature that it produces 3D images that are perspective views of the anatomical structures, with user-controlled means for varying the viewing orientation and location, and also varying the displayed transparency or opacity of various types of tissues, structures, and surfaces in the viewed region of interest. This enables the user to effectively "see through" surfaces and structures in the line of sight of the image to reveal other structures that would otherwise be hidden in that particular view.

Further, the images are generated from the viewpoint of the surgical probe or instrument that is in use, looking from the tip of the instrument along its longitudinal axis. Thus, when an invasive surgical instrument such as a scalpel or forceps is inserted into an incision in the body, the display provides a three dimensional perspective view of anatomical structures from a viewpoint inside the body. These images are all generated in real time "on the fly". Thus, as the instrument is moved or rotated, the position tracking system continually provides data to the computer indicating the location and orientation of the instrument, and the displayed image is continually updated to show the structures toward which the instrument is pointing.

In addition, for probes or instruments being used that are capable themselves of generating images, such as ultrasound probes, endoscopes, or surgical microscopes, the system provides means for integrating these images with those generated from the scan data. The software enables the user to overlay the "actual images" generated by these instruments with the "virtual images" generated from the scan data.

It is an object of this invention to provide a system and method for generating an image in three dimensional perspective of anatomical structures encountered by a surgeon during the performance of surgical procedures.

A second object of this invention is to provide a system and method for generating such an image with user-controlled means for varying the location and orientation of the viewpoint corresponding to the image.

Another object of this invention is to provide a system and method for generating such an image with user-controlled means for varying the opacity of structures and surfaces in the viewed region of interest, so that the displayed image shows structures and features that would be otherwise hidden in a normal view.

Yet another object of this invention is to provide a system and method for generating such an image with a viewpoint located at the tip of the instrument being used by the surgeon in the direction along the longitudinal axis of the instrument.

Still another object of this invention is to provide a system and method for generating such an image in real time, such that the displayed image continually corresponds to the position of the instrument being used by the surgeon.

Yet a further object of this invention is to provide a system and method for comparing and combining such an image with the image produced by an image-generating instrument being used by the surgeon.

These and other objects, advantages, characteristics and features of the invention may be better understood by examining the following drawings together with the detailed description of the preferred embodiments.

DETAILED DESCRIPTION OF THE PREFERRED EMBODIMENTS

Figure 1:
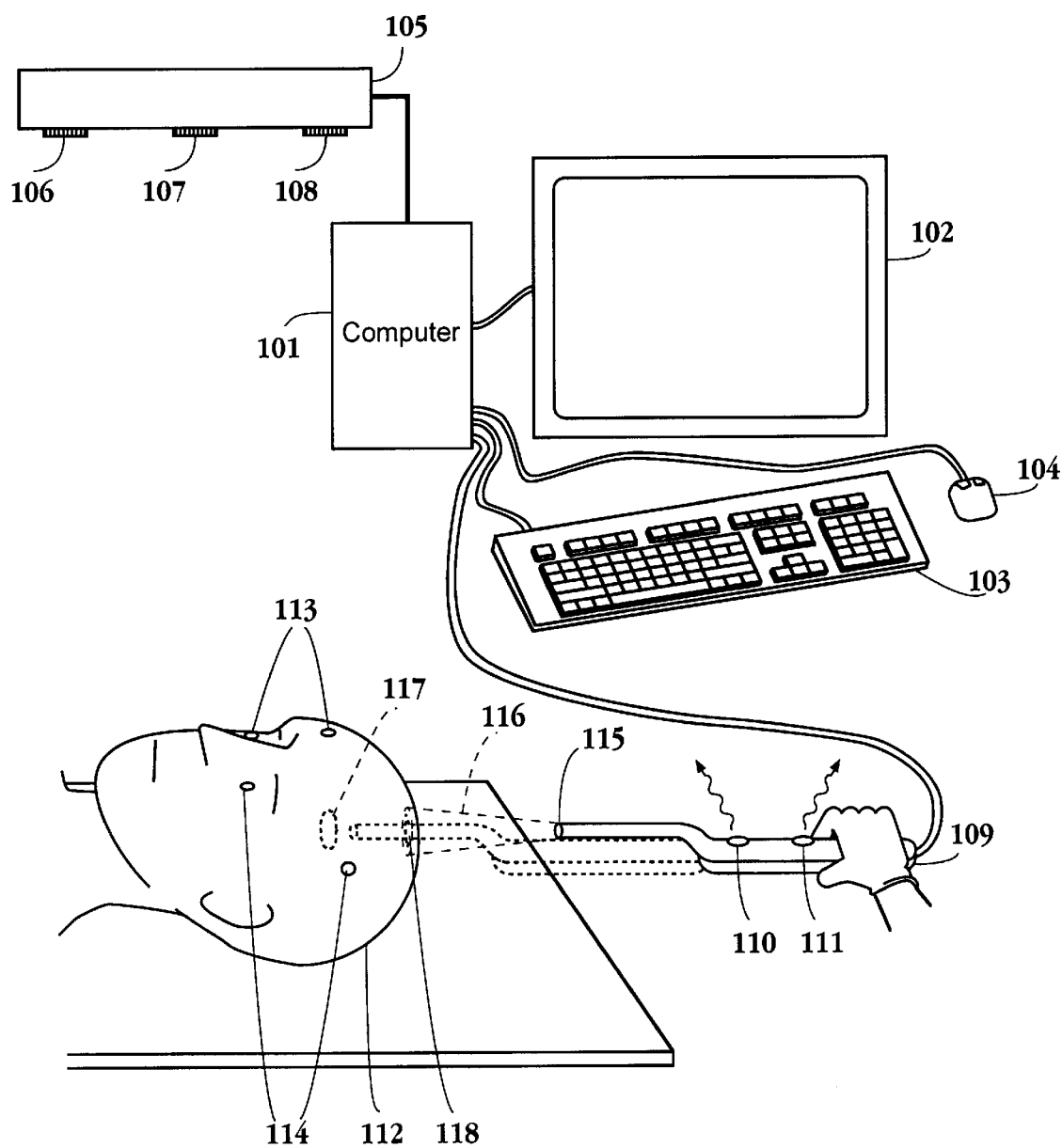
FIG. 1 is a schematic perspective drawing of the apparatus of the present invention in operating room use during the performance of neurosurgical procedures.

FIG. 1 shows the apparatus of the invention as used in performing or planning a neurosurgery operation. In this drawing the patient's head 112, has a tumor or lesion 117, which is the target object of the operation. Fiducial markers 113, 114 are attached to the head to enable registration of images generated by previously obtained scan data according to techniques familiar to persons of ordinary skill in the relevant art. A surgical probe or instrument 109 held by the surgeon is directed toward the tissues of interest. A computer 101 is connected to user input devices including a keyboard 103 and mouse 104, and a video display device 102 which is preferably a color monitor. The display device 102 is located such that it can be easily viewed by the surgeon during an operation, and the user input devices 103 and 104 are placed within easy reach to facilitate use during the surgery. The apparatus further includes a position tracking system, which is preferably an optical tracking system (hereafter "OTS") having a sensing unit 105 mounted overhead in view of the operating table scene, and at least two light emitting diodes (LED's) 110, 111 mounted on the surgical instrument 109. These LED's preferably emit continuous streams of pulsed infrared signals which are sensed by a plurality of infrared sensors 106, 107, 108 mounted in the sensing unit 105 in view of the surgical instrument 109. The instrument 109 and the sensing unit 105 are both connected to the computer 101, which controls the timing and synchronization of the pulse emissions by the LED's and the recording and processing of the infrared signals received by the detectors 106–108. The OTS further includes software for processing these signals to generate data indicating the location and orientation of the instrument 109. The OTS generates the position detecting data on a real time continuous basis, so that as the surgical instrument 109 is moved, its position and orientation are continually tracked and recorded by the sensing unit 105 in the computer 101. The OTS may be preferably of the type known as the "FlashPoint 3-D Optical Localizer", which is commercially available from Image Guided Technologies of Boulder, Colo., similar to the systems described in U.S. Pat. No. 5,617,857 (Chader, et al.) and U.S. Pat. No. 5,622,170 (Schulz) discussed previously. However the invention is not limited to this particular OTS, and other position tracking systems, such as sonic position detecting systems, may also be utilized.

As illustrated in FIG. 1, the surgical instrument 109 is elongated in shape, having a longitudinal axis and tip 115 pointing toward the tissues of interest. The instrument may be an endoscope having a conical field of view 116 that is indicated by dotted lines in FIG. 1. The instrument shown in the Figure is held at a position external to the patient's head. If an incision 118 has been made into the skull, the instrument may be inserted through the incision; this alternative position is shown by dotted lines in FIG. 1. In both positions the instrument is held so that there is an unobstructed line of sight between the LED's 110, 111 and the sensing unit 105. In endoscopic and other optical viewing applications, the instrument may include a laser targeting system (not shown in the drawings) to illuminate and highlight the region under examination.

Figure 2:
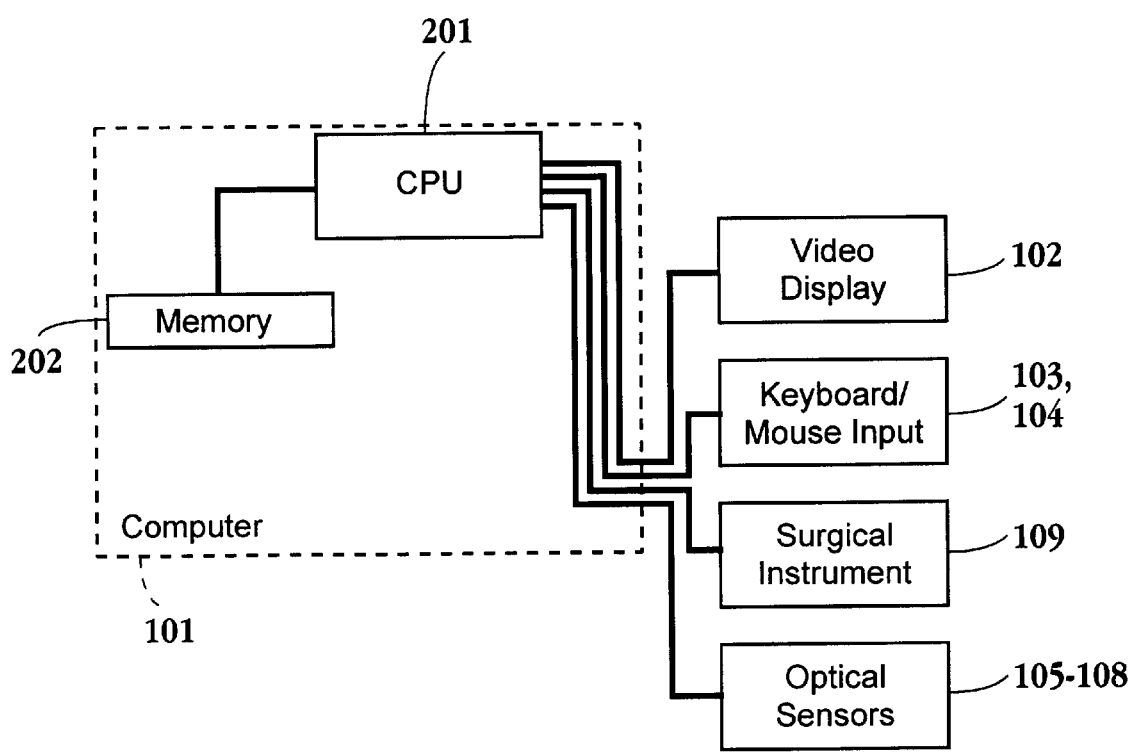
FIG. 2 is a schematic block diagram of the computer system and optical tracking system of the present invention.

FIG. 2 shows a schematic block diagram of the computer system connected to the position tracking system. The computer 101 includes a central processing unit (CPU) 201 communicative with a memory 202, the video display 102, keyboard and mouse 103, 104, optical sensors 106–108, and LED's 110,111 (FIG. 1) mounted on the surgical instrument 109. The computer memory contains software means for operating and controlling the position tracking system. In an alternative preferred embodiment, the OTS components 105–108 may be connected to and controlled by a separate computer or controller which is connected to the computer 101 and provides continual data indicating the position and orientation of the surgical instrument 109.

Figure 3:
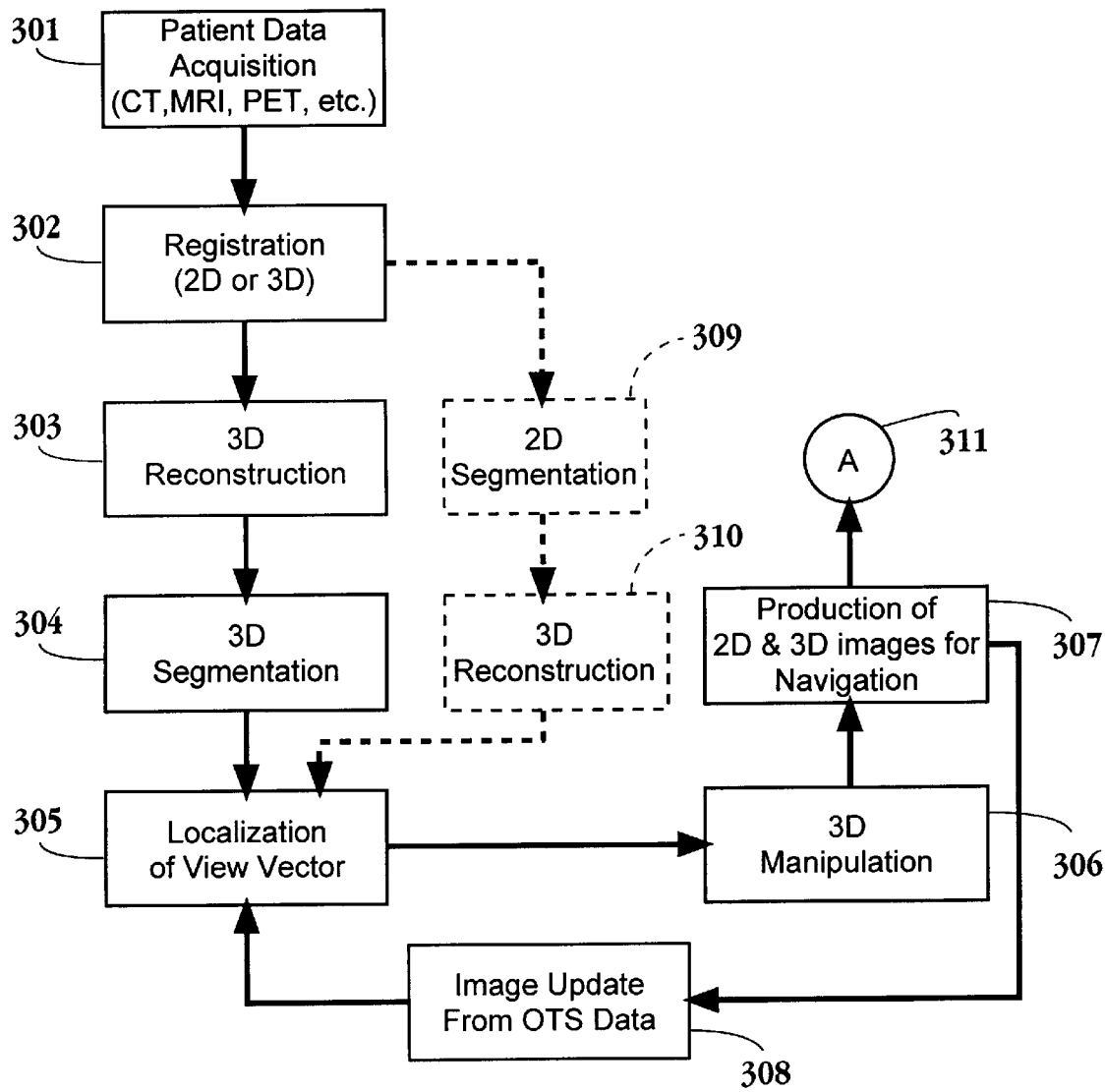
FIG. 3 is a schematic block diagram of the navigation protocol using pre-operative data that is followed in carrying out the method of the present invention.
Figure 4:
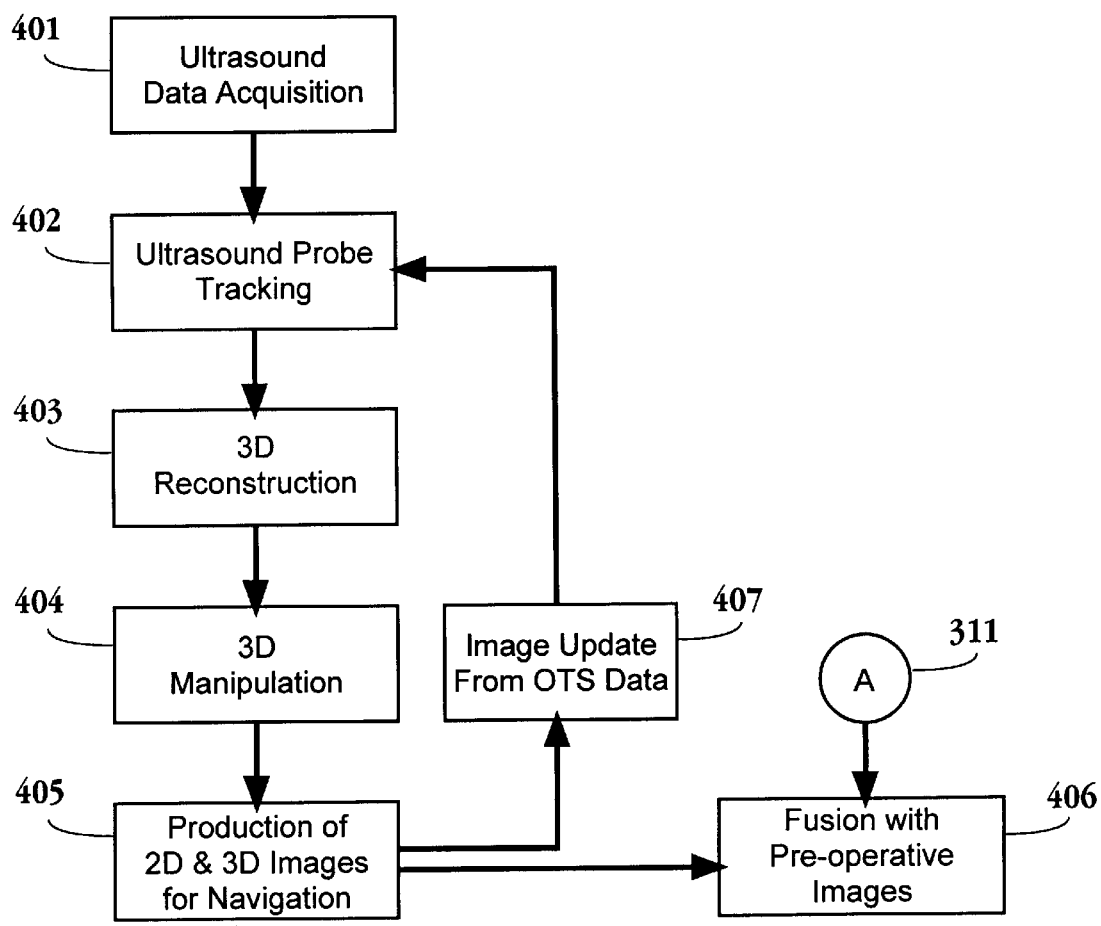
FIG. 4 is a schematic block diagram of the navigation protocol using ultrasound intra-operative data that is followed in carrying out the method of the present invention.
Figure 5:
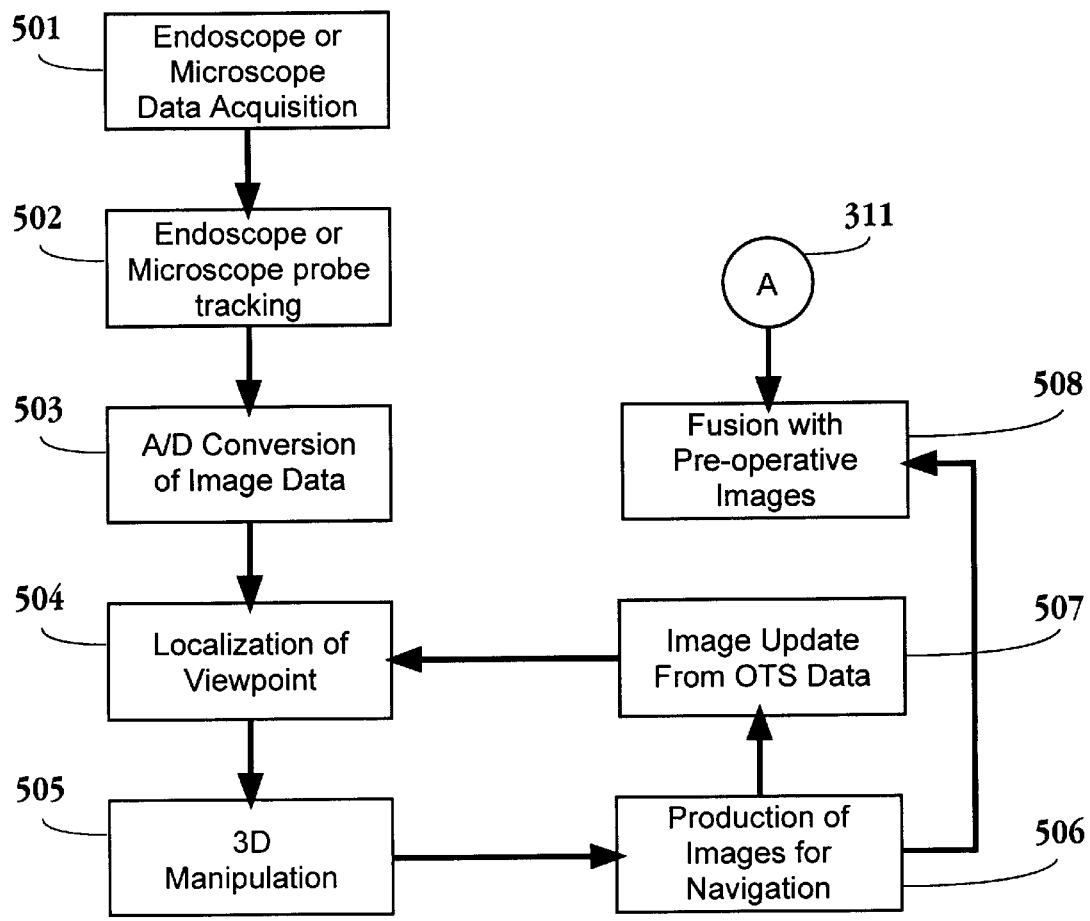
FIG. 5 is a schematic block diagram of the endoscopic protocol that is followed in carrying out the method of the present invention.

The above apparatus is operated to carry out surgical protocols that are illustrated schematically in FIGS. 3–5. FIG. 3 is a schematic block diagram of the protocol for handling pre-operative data ("pre-op protocol") to generate images during surgery according to the present invention. It is assumed that three-dimensional image data of the patient's head have been previously obtained from one or more of the techniques that are known to persons of ordinary skill in the medical imaging arts. Preferably these data are acquired from CT, MIR and/or MRI scan techniques to provide images with improved accuracy and detail, compared to ultrasound scan data for example. The scan data are loaded and stored 301 into the computer memory 202 through additional input means such as disk drives or tape drives, not shown in the drawings.

The patient data is registered 302 according to one of the generally known techniques. This procedure may be either a three-dimensional registration of the entire data set, or a slice-by-slice sequence of two-dimensional registrations. Following the three-dimensional registration, the image is reconstructed 303 in memory, using volumetric or surface rendering to produce an array of 3-dimensional voxel data. Segmentation 304 is then carried out on these data to distinguish various anatomical features, such as different types of material in the head (bone, brain tissue, vascular and ventricular structures, etc.) and the location of surfaces, using one or more of known segmentation techniques. Preferably the segmentation process includes assigning different display colors to different types of structures to facilitate their identification and distinction in a color video display. For example, the vascular system may be displayed in red, the ventricular system may be shown in blue, bones may be colored brown, and so on. In a preferred embodiment these assignments may be varied by the user by means of the keyboard 103 or mouse 104. Also in a preferred embodiment the display opacities may be varied by the user by means of the keyboard 103, mouse 104, or other input device (such as a voice-activated device) to further facilitate their identification and distinction of hidden or obstructed features in the video display. In an alternative protocol in which 2-dimensional registration is carried out, segmentation 309 can be done for each 2-dimensional image sample, and the 3-dimensional data are then reconstructed 310 from the segmented data slices. This alternative protocol is shown by dotted lines in the Figure.

Referring still to FIG. 3, the next phase of the pre-op protocol is to determine the location and orientation of the view vector 305 to define the image to be displayed. This view vector is obtained by querying the OTS to ascertain the current location and orientation of the surgical instrument 109. With this information, the three-dimensional scan data is then manipulated 306 to position and orient the resulting three-dimensional perspective view and to define cutting planes and reference markers in the displayed image indicating and clarifying this view. The manipulated three-dimensional perspective image is then displayed 307 on the video display 102. In addition, other two-dimensional images, such as 2D sectional views for any cutting planes, are preferably also displayed along with the 3D perspective display for purposes of elucidation.

Finally, the pre-op protocol is a continuing loop process in which the OTS is repeatedly queried 308 for changes in the location of the view vector corresponding to changes in the position and orientation of the surgical instrument 109. Thus the displayed images are continually being updated during the surgical procedure, and the resulting displays are constantly refreshed in real time. The image data are also stored or buffered and made available for further use 311 according to subsequent protocols.

The surgical instrument 109 may include an ultrasound transducer located at the tip 115, which itself scans and detects ultrasound imaging data when placed in contact with the patient's head. FIG. 4 is a schematic block diagram showing the intra-operative ("intra-op") ultrasound ("US") protocol for handling the US image data during surgery. Typically the ultrasound transducer is a phased focusing array which generates data from a planar fan-shaped sector of the anatomical region of interest, where the central axis of the transducer lies in the plane of the scan sector which, in this context, is collinear with the longitudinal axis of the surgical instrument 109. By rotating the instrument and transducer about this axis, US scan data is collected and stored 401 for a cone-shaped volume in the region of interest. This cone defines the "field of view" of the transducer scan.

The location and orientation of the transducer is tracked and determined 402 by the OTS, and the US data is used to reconstruct 403 three-dimensional intra-op image data for the region of interest. This data is manipulated 404 in a way analogous to the manipulation 306 of the pre-op data, and then used to generate three-dimensional images 405, together with any desired corresponding two-dimensional images of the ultrasound data. These intra-op images are fused 406 with the pre-op image generated by the pre-op protocol 311, and the composite images are further displayed. Finally, the OTS is continually strobed 407, and the ultrasound images are constantly refreshed.

FIG. 5 is a schematic block diagram of the intra-op protocol in which an endoscope is placed at the tip 115 of the surgical instrument 109. This protocol is also applicable for procedures utilizing a surgical microscope in place of the endoscope. Image data is acquired 501, using a CCD camera or other known technique, representing a 2-dimensional image in a plane orthogonal to the line of sight of the endoscope or microscope, which in this context is the longitudinal axis of the surgical instrument 109. The location and orientation of the instrument is tracked and determined 502 by the OTS, and analog-to-digital ("A/D") conversion 503 is carried out on the data. The location of the viewpoint is determined 504 from the OTS data, and the endoscope or microscope image data is manipulated 505 to generate the desired image 506 for display. These intra-op images are fused 508 with the pre-op images generated by the pre-op protocol 311, and the composite images are further displayed. Finally, the OTS is continually strobed 507, and the ultrasound images are constantly refreshed.

Figure 6:
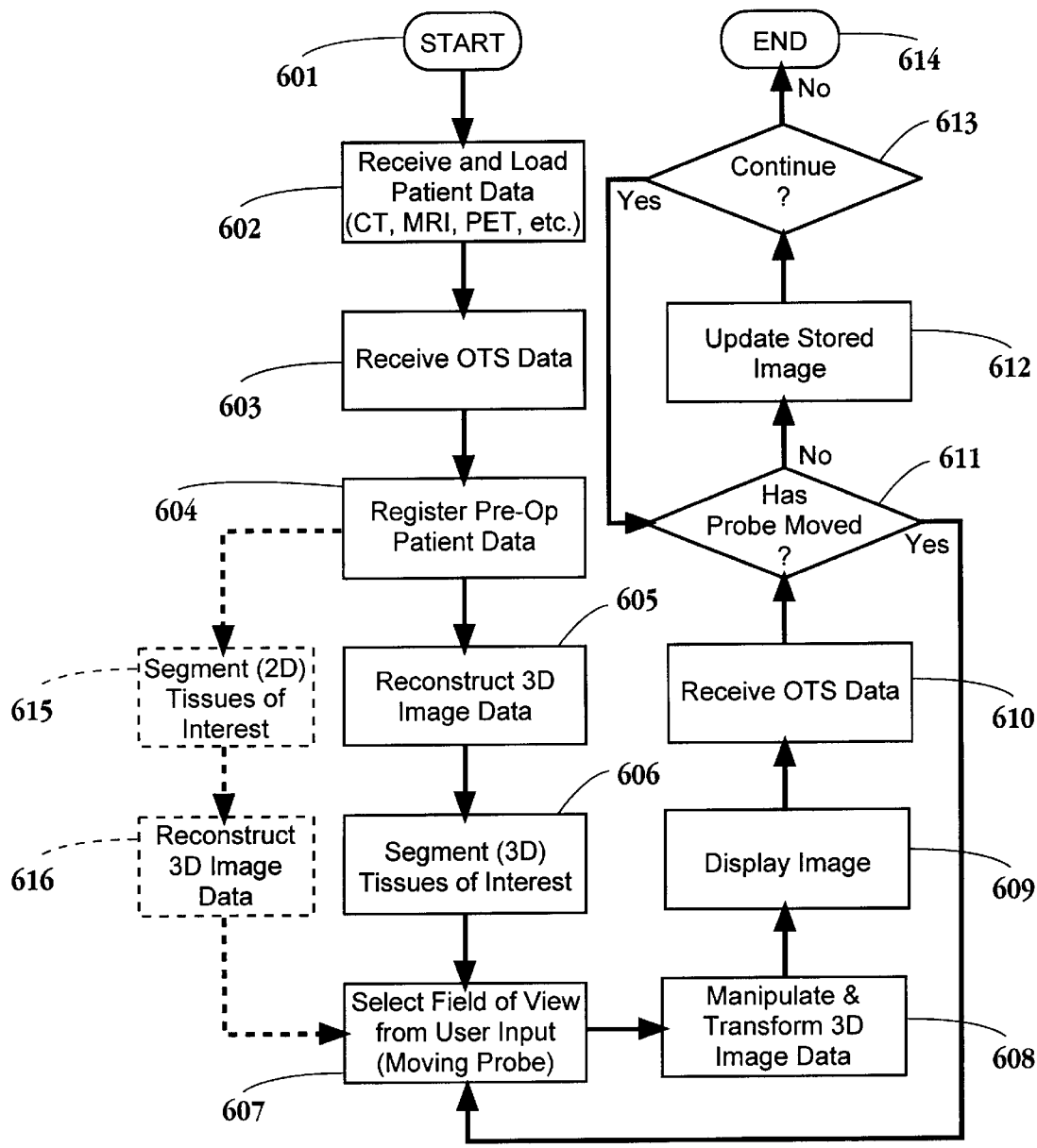
FIG. 6 is a schematic flow chart of the pre-operative computer program that implements the pre-operative protocol of the present invention.

The foregoing protocols are implemented by program modules stored in the memory 202 of the computer 101. FIG. 6 is a schematic block diagram of a flow chart for a program that implements the pre-op protocol. The program starts 601 by causing the computer to receive and load 602 previously obtained scan data for the patient, such as MRI or CT data. The computer further reads data from the OTS 603 to register the scanned patient data 604. For 3D volumetric rendering, the scanned data is used to reconstruct image data 605 in three dimensions, and segmentation 606 is carried out on this reconstruction. In an alternative embodiment, shown by dotted lines in the Figure, segmentation is carried out on 2D slices 615, and these segmented slices are then reconstructed into the full 3D image data.

The program next reads input data from the keyboard 103 or mouse 104 to enable the user to select a field of view for image displays 607. The image data is then manipulated and transformed 608 to generate the requested view, along with any selected reference markers, material opacities, colors, and other options presented to the user by the program. In addition, the user may request a 3D display of the entire head, together with a superimposed cone showing the field of view for an endoscope, microscope, ultrasound transducer, or other viewing device being used during the surgery. The resulting manipulated image is then displayed 609 preferably in color on the video display 102. The computer next reads the OTS data 610 and determines 611 whether the surgical instrument has moved. If so, program control returns to the selection of a new field of view 607 and the successive operations 608–610 shown in FIG. 6. If the position of the instrument has not changed, the displayed image is stored 612, refreshing any previously stored display image. The program further looks for requests from the user 613 whether to discontinue operation, and it there are no such requests, the operations 611 and 612 are repeated. Thus the computer remains in a loop of operations until the user requests termination 614.

Figure 7:
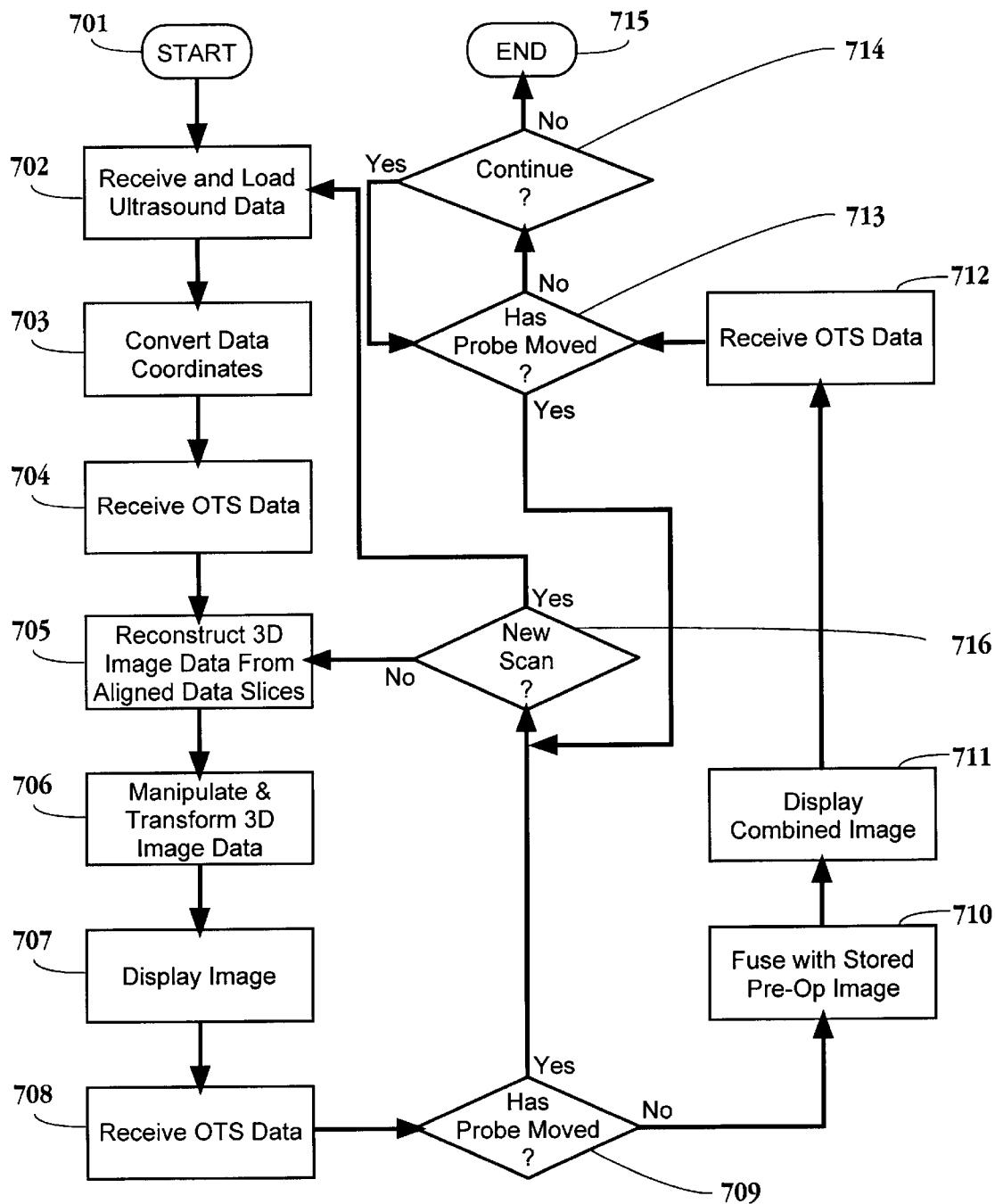
FIG. 7 is a schematic flow chart of the intra-operative ultrasound computer program that implements the ultrasound protocol of the present invention.

FIG. 7 is a schematic block diagram of a flow chart for a program that implements the ultrasound intra-op protocol. The program starts 701 by causing the computer to receive and load the data from a US transducer at the tip 115 of the surgical instrument 109. Such data is produced normally using polar or spherical coordinates to specify locations in the region of interest, and the program converts 703 this data preferably to Cartesian coordinates. Next, OTS data is read 704 to determine the position and orientation of the surgical instrument 109, and US data from the aggregation of aligned data slices is utilized to reconstruct 3D image data 705 representing the US scan data. This image data is manipulated and transformed 706 by the program in a manner similar to the manipulation 608 of the pre-op data 608, and the resulting image is displayed 707.

Similarly to the pre-op program shown in FIG. 6, the OTS is queried 709 to determine whether the surgical instrument has moved 713, and if so a new US display image is constructed. In a preferred embodiment, the program queries the user 716 whether to carry out another US scan of the region of interest. If so, program control returns to the operation 702 in FIG. 7 and fresh US data is obtained by the US transducer. If another scan is not requested 716, the program returns to operation 705 and a new 3D image is reconstructed from the present US scan data.

If the OTS query 709 determines that the surgical instrument has not moved since the last query, the US image is fused 710 with the pre-op image obtained by the program shown in FIG. 6, and the combined image is displayed 711. The OTS is again queried 712 to determine 713 whether the surgical instrument has moved. If so, the program returns to the new scan user query 716. Otherwise the program further looks for requests from the user 714 whether to discontinue operation, and if there are no such requests, the operation 713 is repeated. Thus the computer remains in a loop of operations until the user requests termination 715, similarly to the pre-op program of FIG. 6.

Figure 8:
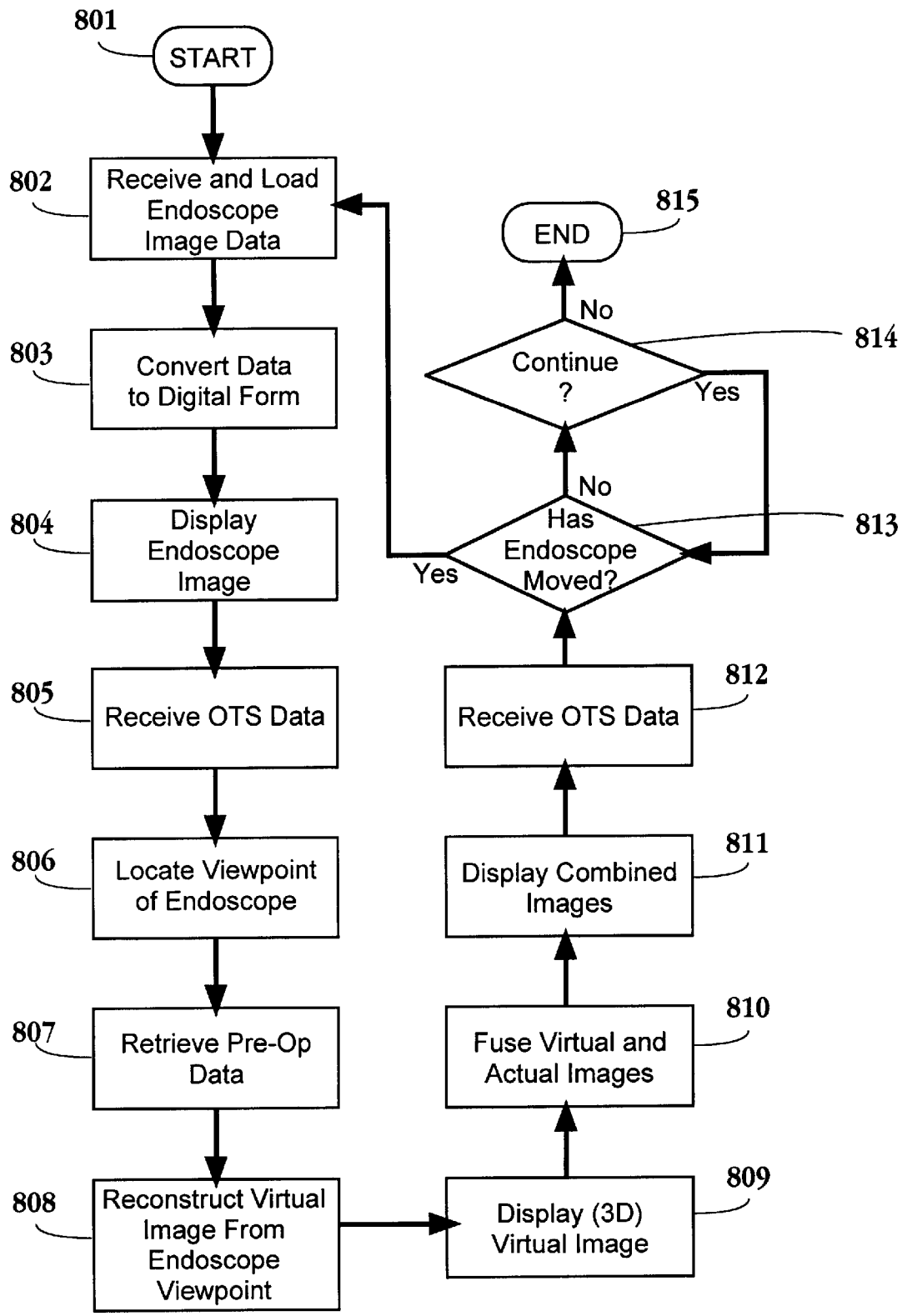
FIG. 8 is a schematic flow chart of the intra-operative endoscope computer program that implements the endoscope protocol of the present invention.

The endoscope/microscope intra-op protocol is implemented preferably by the endoscope intra-op program having a flow chart shown in schematic block diagram form in FIG. 8. Upon starting 801, the program causes the computer to receive and load image data from the endoscope 802. This data is digitized 803 and preferably displayed 804 on the video display 102. The OTS is queried 805 to receive information determining the location and orientation of the endoscope 806. Using this information, the pre-op data obtained by the pre-op program illustrated in FIG. 6 is retrieved 807, and utilized to reconstruct a 3-dimensional virtual image 808 from the viewpoint of the endoscope. This image is displayed 809, in a manner similar to the 3D display of images by the pre-op program illustrated in FIG. 6. This image is fused 810 with the endoscope image displayed in operation 804, and the combined image is also displayed 811. The OTS is then strobed 812 to determine 813 whether the endoscope has moved since the last query, and if so, program control returns to the operation 802 which refreshes the image data received by the endoscope. Otherwise the program further looks for requests from the user 814 whether to discontinue operation, and if there are no such requests, the operation 813 is repeated. Thus the computer remains in a loop of operations until the user requests termination 815, similarly to the pre-op and intra-op programs of FIGS. 6 and 7.

The foregoing program modules may be designed independently, and they can be configured also to run independently. Thus, the pre-op program may be completed, followed by running of either or both of the intra-op programs. Preferably, however, these programs operate in parallel during surgery so that the pre-op data images and intra-op data images are all continually refreshed as the operation proceeds. Known methods for parallel execution of programs may be utilized to accomplish this result.

The above programs are carried out preferably on a computer 101 that is adapted for computer graphics applications. Suitable computers for these programs are commercially available from Silicon Graphics, Inc. of Mountain View, Calif. Graphics software modules for most of the individual image processing operations in the above programs are also available from Silicon Graphics, Inc. as well as other sources.

Figure 9:
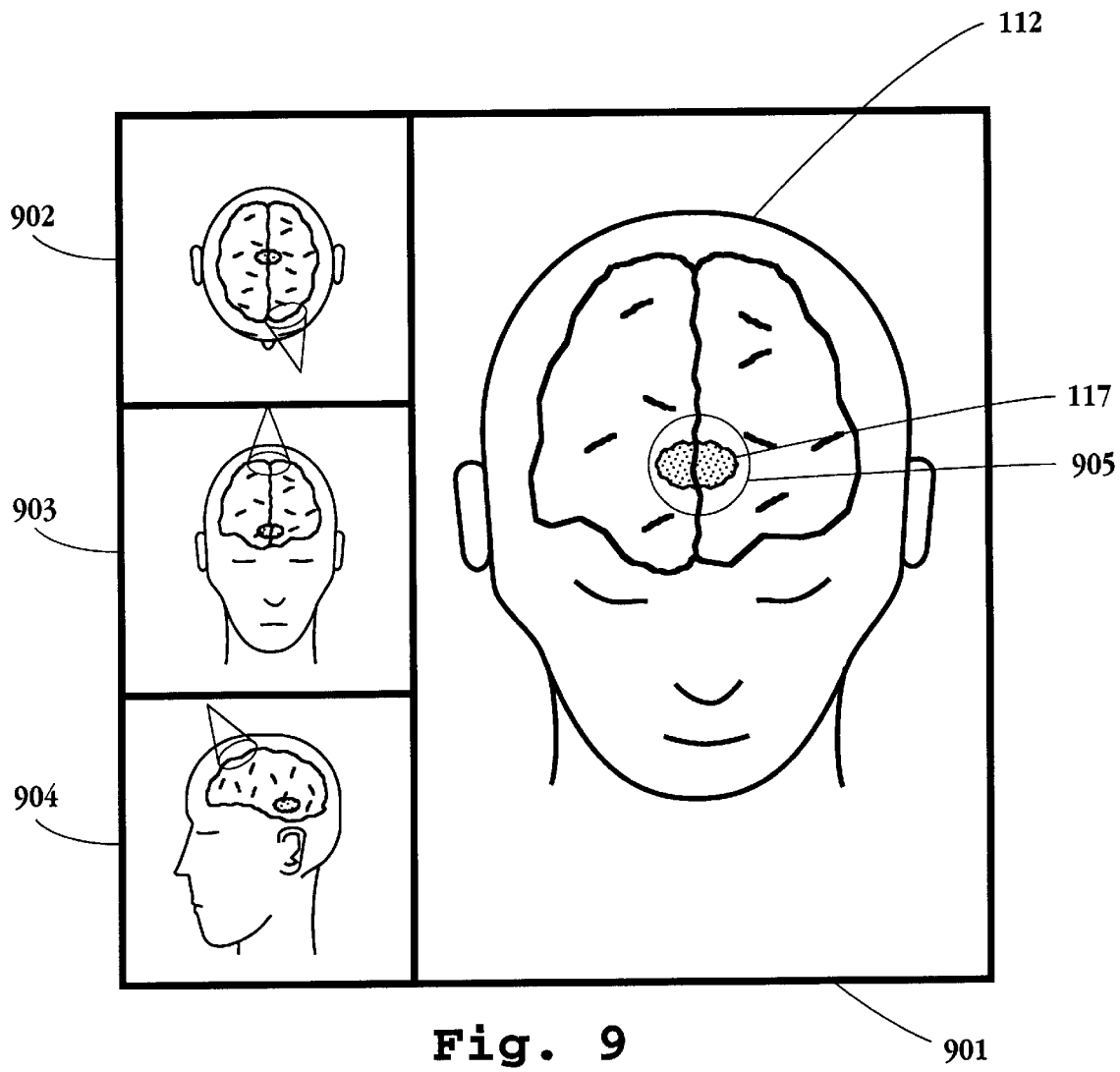
FIG. 9 is a drawing of a display generated according to the present invention, showing axial, coronal, and sagittal views of a head, together with a three-dimensional perspective view of the head taken from an exterior viewpoint.

Referring now to FIG. 9, the drawing shows a highly simplified sketch of a three-dimensional image display 901 obtained by the above system with the surgical probe 109 of FIG. 1 in the position illustrated, pointing toward the target lesion or tumor 117 inside the patient's head 112. The display 901 is a perspective view from the tip 115 of the probe 109 in FIG. 1. This display is continuously refreshed, so that as the probe 109 is moved the displayed image 901 immediately changes. It will be noted that, although the probe 109 in FIG. 1 is shown entirely outside the patient's head, the display 901 shows internal anatomical structures such as the brain and the target lesion 117. With the present system, the display characteristics can be adjusted in real time to emphasize or de-emphasize the internal structures. These structures may be distinguished by displays with different colors for different types of material. Also, the display opacity of the skin, skull, and brain tissue may be reduced to provide or emphasize further structural details regarding the target lesion 117. In short, the display 901 effectively equips the surgeon with "X-ray eyes" to look at hidden structures through obstructing surfaces and objects. With this display, the entire internal structure of the head may be examined and studied to plan a surgical trajectory before any incision is made. Furthermore, if the surgical instrument 109 in FIG. 1 is a scalpel, the display 901 allows the surgeon to see any structures immediately behind a surface prior to the first incision. FIG. 9 shows also the conventional axial 902, coronal 903 and sagittal 904 2D displays for purposes of further clarification and elucidation of the region under examination.

When the surgical instrument 109 is an endoscope or US transducer, the field of view 116 is also indicated in the display 901 by the quasi-circular image 905 indicating the intersection of the conical field of view 116 with the surface of the skin viewed by the endoscope 109. This conical field of view is also superimposed, for completeness, in the 2D displays 902–904. In a preferred embodiment, displays are also presented showing the actual image seen by the endoscope in the field of view 905, and the 3D perspective image for the same region in the field of view 905; these auxiliary displays are not shown in the drawings. Similar auxiliary displays are preferably included when the instrument 109 is an ultrasound transducer.

Figure 10:
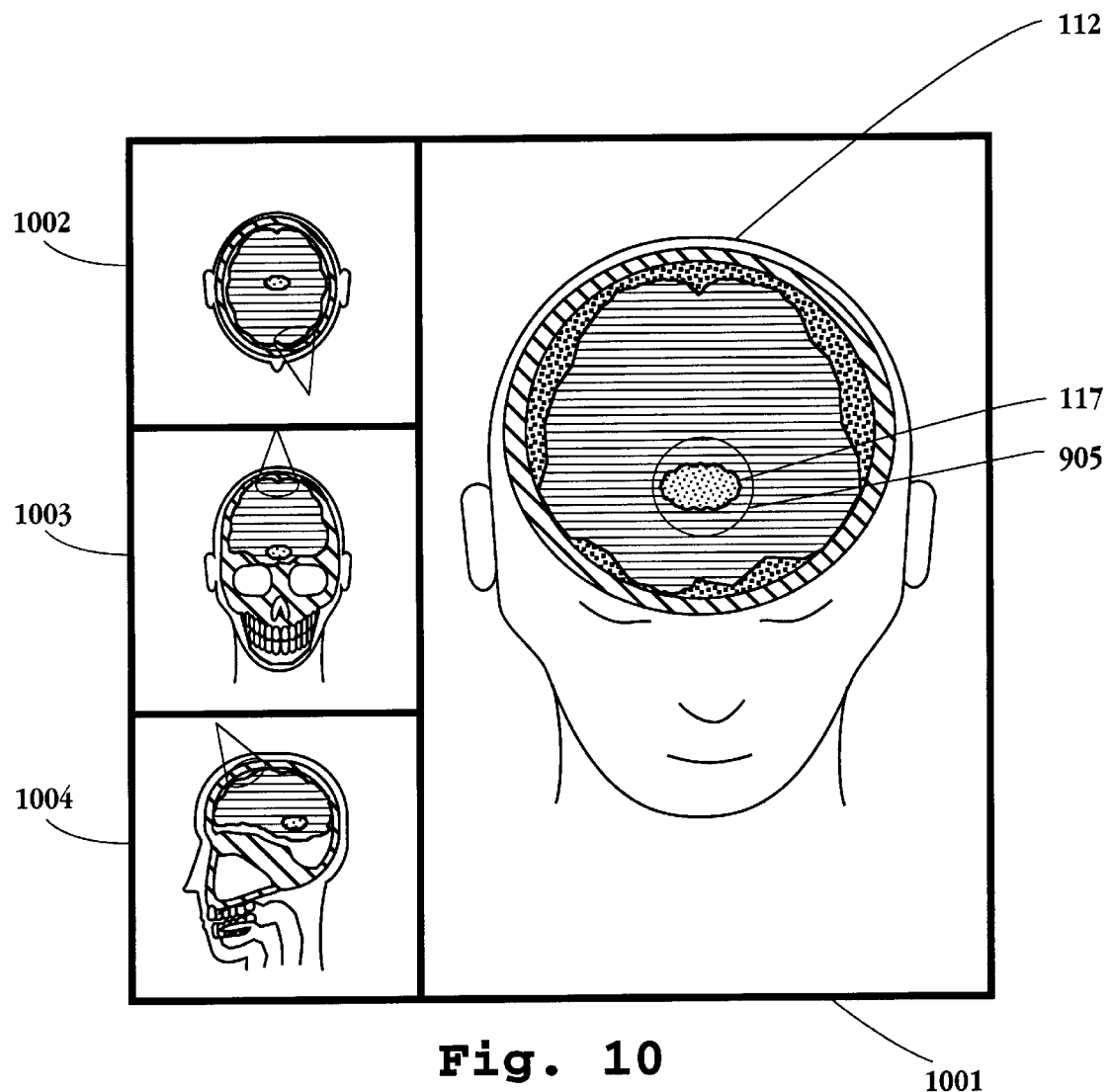
FIG. 10 is a drawing of a display generated according to the present invention, showing sectional axial, coronal, and sagittal views of a head, together with a three-dimensional perspective view of the head taken from an interior viewpoint.

After an incision 118 has been made in the patient's head, the endoscope may be inserted to provide an internal view of the target anatomy. Referring now to FIG. 10, the drawing shows a highly simplified sketch of a three-dimensional image display 1001 obtained by the above system with the endoscope 109 of FIG. 1 in the alternative position shown by the dotted lines, pointing toward the target lesion or tumor 117. The display 1001 has been manipulated to provide a three-dimensional sectional view with a cutting plane passing through the tip 115 of the endoscope 109 and orthogonal to its axis. Again, the endoscope field of view 905 is indicated in the display, and in a preferred embodiment auxiliary displays are also presented showing the actual image seen by the endoscope in the field of view 905, and the 3D perspective image for the same region in the field of view 905; these auxiliary displays are also not shown in FIG. 10. This Figure further preferably includes also the conventional axial 1002, coronal 1003 and sagittal 1004 2D displays for purposes of further clarification and elucidation.

Figure 11A:
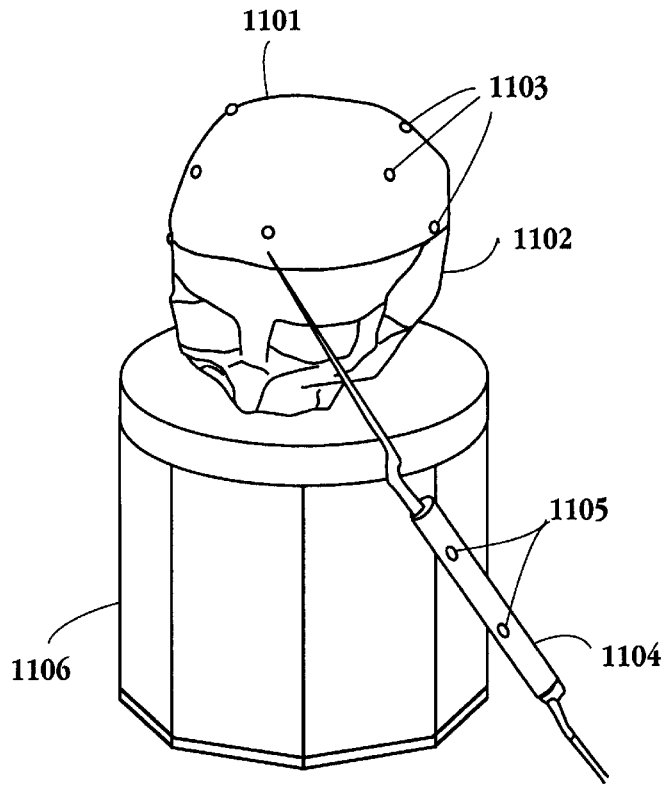
FIG. 11a is a drawing of a plastic model of a human skull and a surgical probe that has been used to demonstrate the present invention.
Figure 11B:
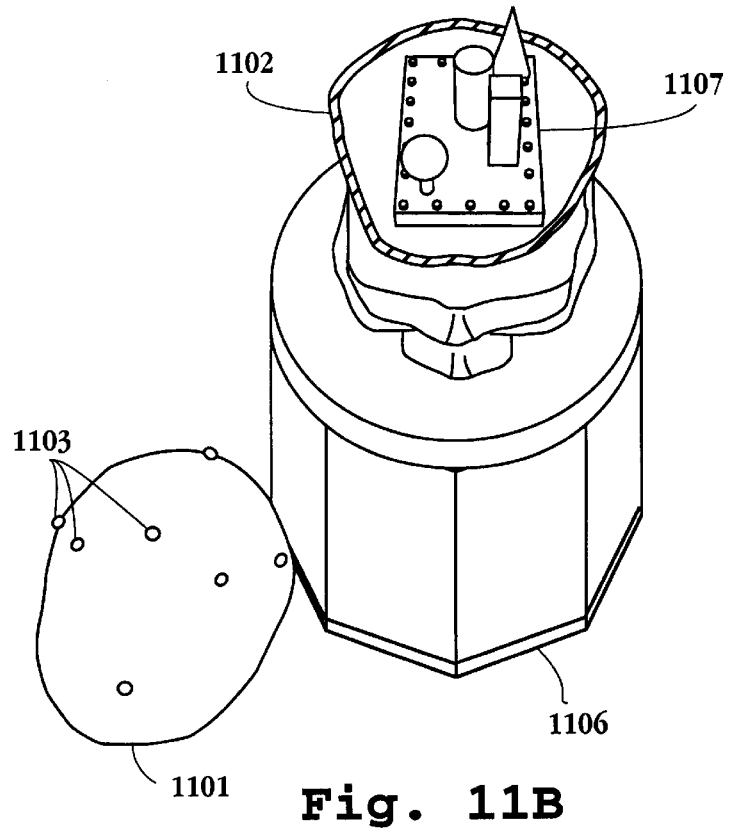
FIG. 11b is another drawing of the model skull of FIG. 11a, with the top of the skull removed to show model internal structures for demonstration purposes.

FIGS. 11a, 11b, 12 and 13 illustrate further the three-dimensional displays that are produced by a preferred embodiment of the present invention. Referring to FIGS. 11a, 11b, a plastic model of a skull has been fabricated having a base portion 1102 and a removable top portion 1101. These Figures show the model skull 1101, 1102 resting on a stand 1106. FIG. 11a also shows a pointer 1104 with LED's 1101 connected to an OTS (not shown in the drawing) that has been used to generate displays according to the invention. A plurality of holes 1103 in the top portion 1101 are provided, which allow the pointer 1104 to be extended into the interior of the skull. FIG. 11b shows the skull with the top portion 1103 removed. A plastic model of internal structures 1107 is fabricated inside the skull; these internal structures are easily recognizable geometric solids, as illustrated in the Figure.

Figure 12A:
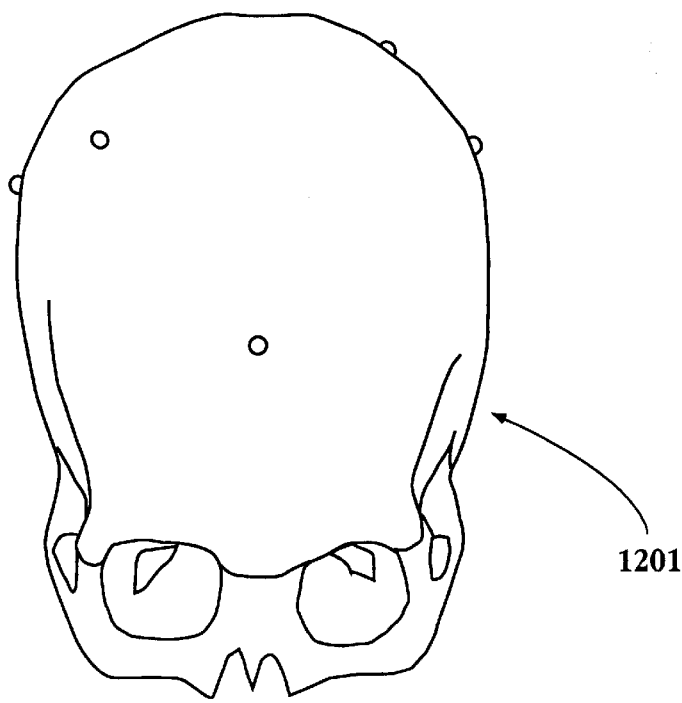
FIG. 12 is a simplified reproduction of two displays produced by the present invention for the model skull shown in FIGS. 11a, 11b.
Figure 12B:
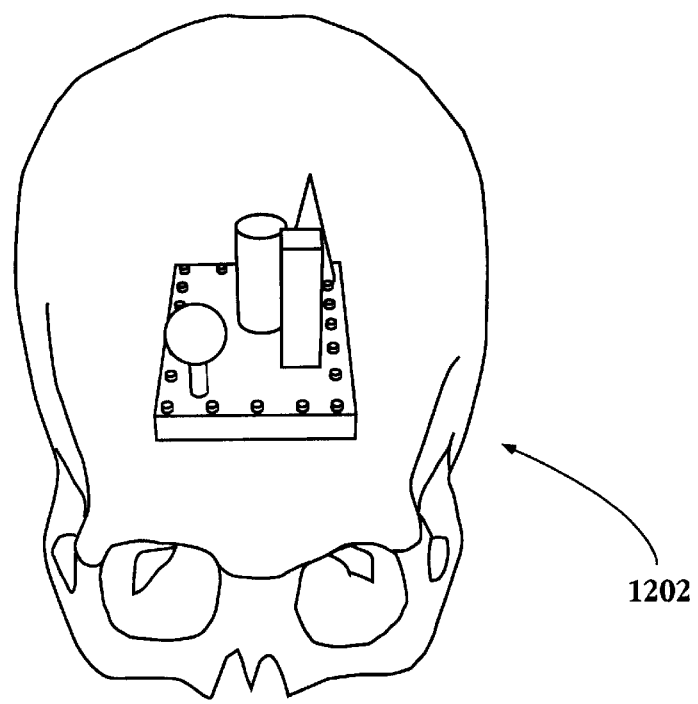
Figure 13A:
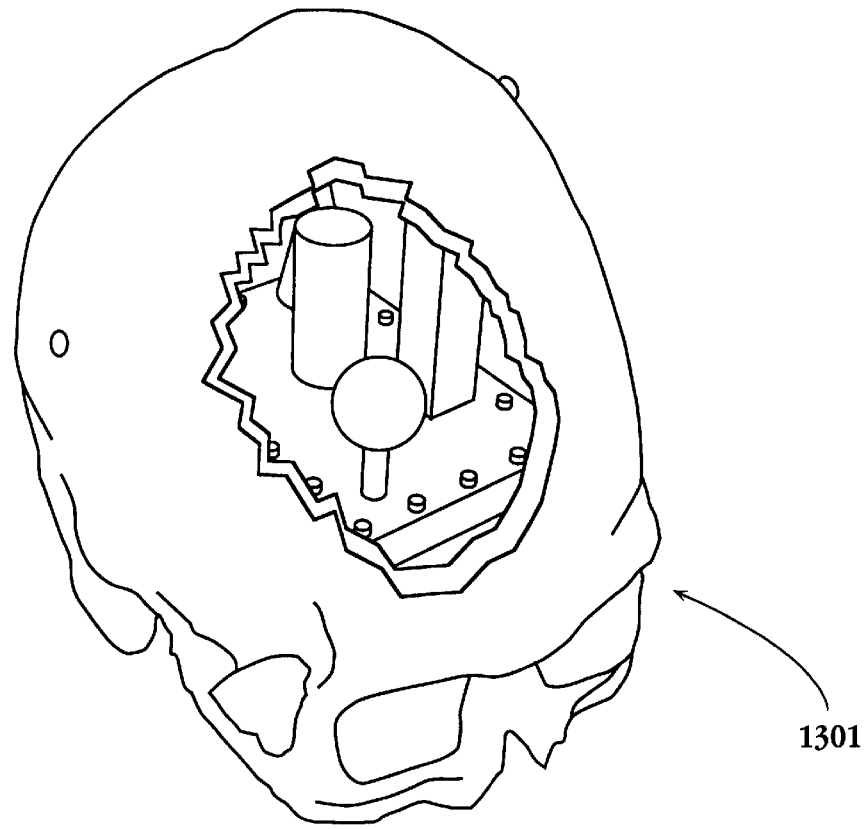
FIG. 13 is a simplified reproduction of two further displays of the invention for the skull in FIGS. 11a, 11b.
Figure 13B:
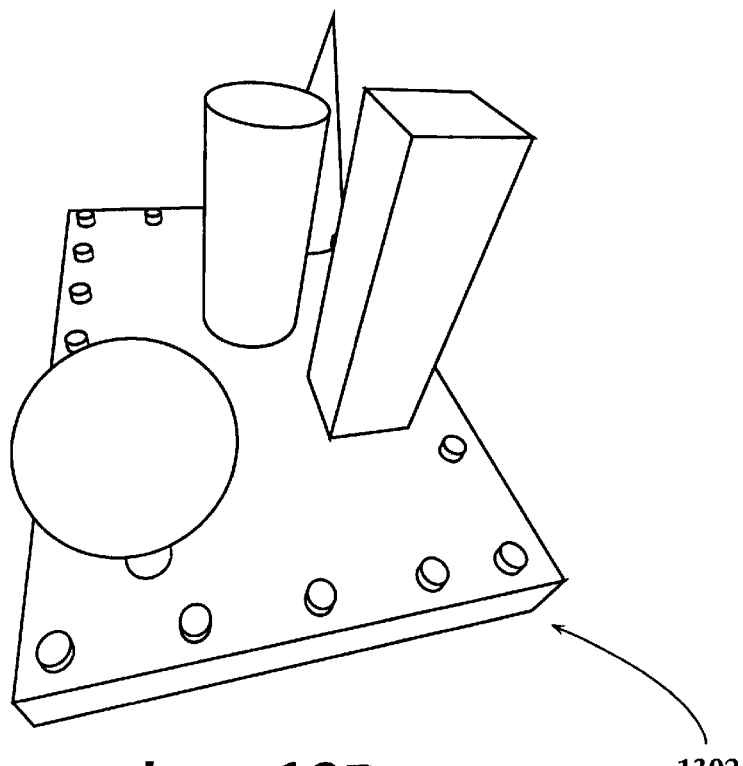
Figures 14B, 14C:
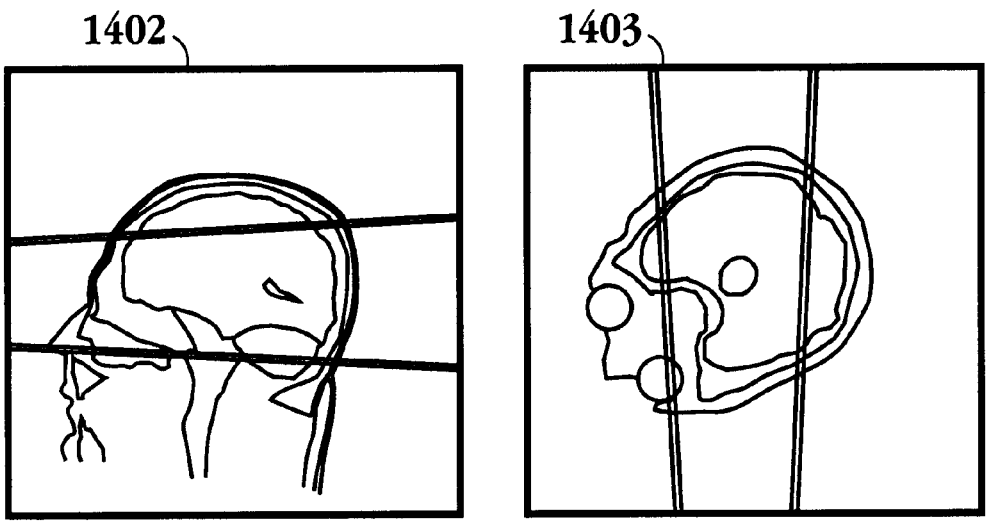
FIG. 14 is a reproduction of a composite display produced by the present invention for an actual human head.
Figure 14A:
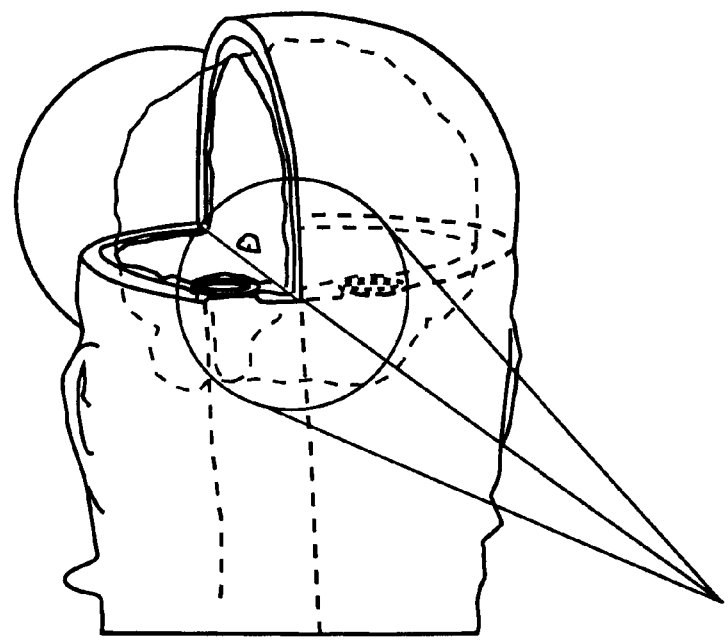
Figure 14D:
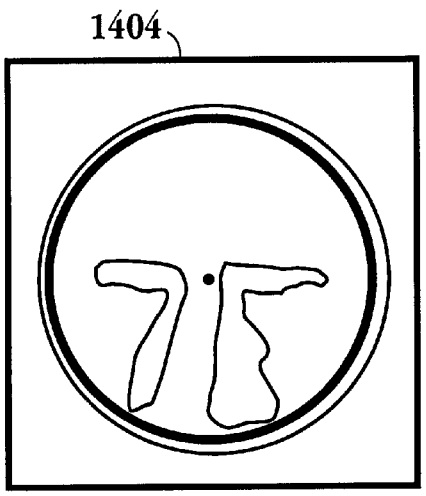
Figure 14E:
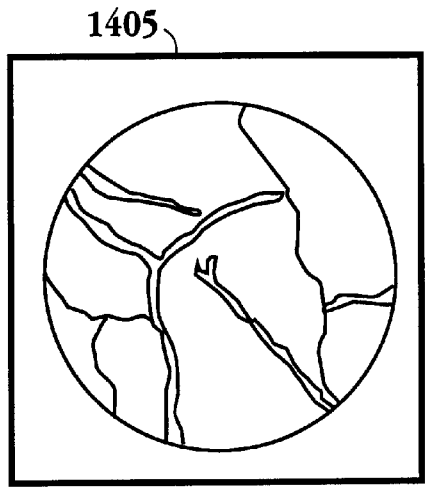
Figure 14F:
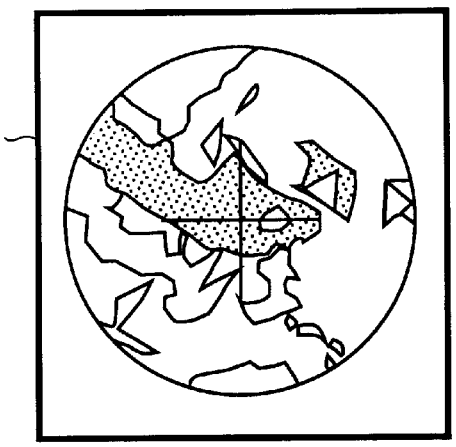
Figure 14G:
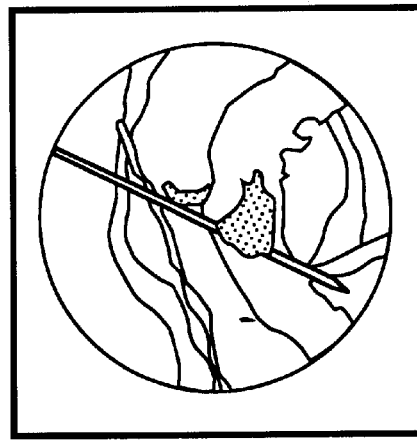
Figure 14H:
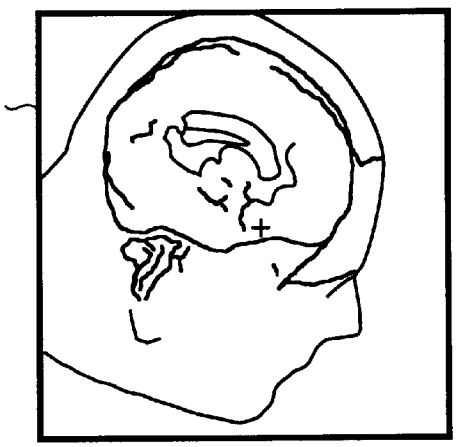
Figure 14I:
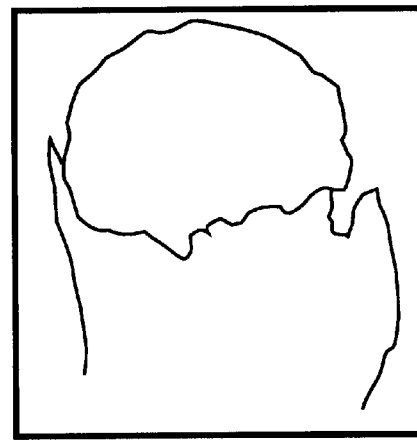

The skull of FIGS. 11a, 11b has been scanned to generate "pre-op" image data, which has been utilized to produce the displays shown in FIGS. 12, 13. FIG. 12 is a composite of two displays 1201, 1202 of the skull with the pointer 1104 directed toward the skull from a top center external location, similar to the location and orientation of the pointer shown in FIG. 1. The display 1201 is a three-dimensional perspective view from this pointer location. The display 1202 is the same view, but with the display opacity of the skull material reduced. This reduced opacity makes the internal structure 1107 clearly visible, as shown in the Figure. During actual use, the system enables the surgeon to vary this opacity in real time to adjust the image so that both the skull structure and the internal structure are visible in the display in various proportions.

It will be noted that the surface contour lines shown in the display 1201 are produced by the finite size of the rendering layers or voxels. These contour lines may be reduced by smoothing the data, or by reducing the sizes of the voxels or layers.

FIG. 13 is a composite of two further displays with the pointer 1104 moved to extend through one of the openings 1103. Display 1302 is the view from the tip of the pointer inside the skull. Display 1301 is a view of the entire structure from outside the skull along the pointer axis; in other words, display 1302 is substantially a magnification of part of display 1301. Display 1301 shows the skull with a portion cut away by a cutting plane through the tip of the pointer, perpendicular to the pointer axis. Both of these displays clearly illustrate the perspective nature of the three-dimensional displays generated by the present invention.

Finally, FIG. 14 is a simplified composite of displays generated by the system for an actual human head. Display 1401 is a perspective view of the entire head with a cutaway portion defined by orthogonal cutting planes as shown. This display also shows the field of view of an endoscope pointing toward the head along the intersection line of the two cutting planes, with the tip of the endoscope at the apex of the cone. Display 1402 shows the two-dimensional sectional view produced by the vertical cutting plane, and display 1403 shows the corresponding sectional view produced by the horizontal cutting plane. Furthermore, the images in displays 1402 and 1403 are also transformed (rotated and magnified) and superimposed on the three-dimensional image in display 1401.

Both of these displays indicate also the intersection of the cutting planes with the conical field of view. Display 1404 is the actual image seen by the endoscope. Display 1405 is a virtual perspective view of the endoscope image reconstructed from scan data by volume rendering in accordance with the present invention. Display 1406 is a virtual perspective view of the image from the endoscope viewpoint with a narrower field of view, reconstructed from scan data by surface rendering in accordance with the present invention. This display 1406 would be used with a surgical probe in planning a surgical trajectory. Display 1407 is a magnification of 1406 produced at display 1405 at a wider field of view, showing the virtual image that would be seen through a microscope. Finally, display 1408 is a segmented three-dimensional perspective view of the entire head from the scan data utilizing surface rendering, and display 1409 is the same view with volume rendering. FIG. 14 illustrates the rich variety and versatility of the displays that are possible with the present system. All of these displays are presented to the surgeon in real time, simultaneously, and can be varied on line.

It is apparent from the foregoing description that this invention provides improved means for navigating through the anatomy during actual surgical procedures. The system enables the surgeon to select and adjust the display with the same tool that is being utilized to perform the procedure, without requiring extra manual operations. Since the displays are provided immediately in real time, the imaging does not require any interruption of the procedure. In addition, the virtual images provided by this system are continuously correlated with the images that are obtained through conventional means.

It will be further appreciated by persons of ordinary skill in the art that the invention is not limited in its application to neurosurgery, or any other kind of surgery or medical diagnostic applications. For example, systems implementing the invention can be implemented for actual nautical or aviation navigation utilizing information from satellites to obtain the "pre-op" scan data. The pointing device can be implemented by the vessel or aircraft itself, and the video display could be replaced by special imaging goggles or helmets.

The foregoing description of the preferred embodiments of the invention has been presented solely for purposes of illustration and description, and is not exhaustive or limited to the precise forms disclosed. Many modifications and variations are possible in light of the above teaching. The spirit and scope of the invention are to be defined by reference to the following claims, along with their full scope of equivalents.

What is claimed is:

1. A method for facilitating a diagnostic or surgical procedure involving a subsurface target site in a patient, comprising
   (a) acquiring volumetric scan data of the target site,
   (b) moving a medical instrument to a selected orientation with respect to the patient target site;
   (c) determining the orientation of the medical instrument with respect to the patient target site;
   (d) selecting a field-of-view angle,
   (e) constructing from the volumetric scan data, a volumetric perspective image of the target site, as seen from the orientation of the medical instrument, at the selected field-of-view angle, and
   (f) displaying said perspective image to a person manipulating the instrument, in real time, allowing the person to visualize subsurface target structure at the selected field-of-view angle, as the medical instrument is moved with respect to the patient target site.

2. The method of claim 1, wherein said medical instrument is an endoscope operable to generate a visual image from the perspective of a distal-end lens.

3. The method of claim 2, wherein said displaying includes simultaneously displaying the image produced by the endoscope and the perspective image generated by said constructing.

* * * * *